United States Patent
Loth et al.

(10) Patent No.: US 9,067,051 B2
(45) Date of Patent: Jun. 30, 2015

(54) VALVE DEVICE FOR CONTROLLING A FLOW OF A FLUID THROUGH A FLUID CHANNEL, ARRANGEMENT AND MULTI-WAY VALVE DEVICE

(75) Inventors: Andreas Loth, Berlin (DE); Florian Buehs, Berlin (DE)

(73) Assignee: Technische Universitat Berlin, Berlin (DE)

( * ) Notice: Subject to any disclaimer, the term of this patent is extended or adjusted under 35 U.S.C. 154(b) by 0 days.

(21) Appl. No.: 13/701,312

(22) PCT Filed: Jun. 1, 2011

(86) PCT No.: PCT/DE2011/075127
§ 371 (c)(1),
(2), (4) Date: Jan. 14, 2013

(87) PCT Pub. No.: WO2012/022314
PCT Pub. Date: Feb. 23, 2012

(65) Prior Publication Data
US 2013/0118619 A1    May 16, 2013

(30) Foreign Application Priority Data
Jun. 2, 2010 (DE) .......................... 10 2010 017 216

(51) Int. Cl.
*F16K 7/06* (2006.01)
*A61M 39/28* (2006.01)
(Continued)

(52) U.S. Cl.
CPC ......... *A61M 39/284* (2013.01); *A61M 37/0076* (2013.01); *A61M 39/223* (2013.01); *F16K 7/045* (2013.01); *A61M 2039/226* (2013.01)

(58) Field of Classification Search
USPC ...................................... 251/4, 7, 9; 604/250
See application file for complete search history.

(56) References Cited

U.S. PATENT DOCUMENTS 2,816,514 A * 12/1957 Freese ........................... 417/412
2,842,331 A *  7/1958 Anderson ........................ 251/6
(Continued)

FOREIGN PATENT DOCUMENTS

| DE | 1707336 | 9/1955 |
| DE | 2353624 | 5/1974 |

(Continued)

*Primary Examiner* — John K Fristoe, Jr.
*Assistant Examiner* — Frederick D Soski
(74) *Attorney, Agent, or Firm* — Harness, Dickey

(57) ABSTRACT

The invention relates to a valve device for controlling a flow of a fluid through a fluid channel, having a tube (2) made of a flexible material, in which a section of a fluid channel is formed, a valve component (1) assigned to the tube (2), a cantilevered arm (8), which is designed to be reversibly displaceable on the valve component (1) against a restoring force supplied at least partially by the cantilevered arm (8) itself, a squeeze element (10), which is arranged on a distal end of the cantilevered arm (8) for support of the cantilevered arm (8) on the valve component (1) and is configured to control a flow of a fluid through the fluid channel by pressing against an outside surface of the tube (2), optionally up to the closing of the fluid channel, and an actuator (11) which is configured to displace the squeeze element (10) in various control directions against the restoring force on the cantilevered arm (8), so that the pressure of the squeeze element (10) on the outside surface of the tube (2) and thereby the flow through the fluid channel can be regulated. In addition, the invention also relates to a system having at least one valve device and a pressure-applying device as well as a multi-way valve device having multiple valve devices.

14 Claims, 9 Drawing Sheets

Figure 1:
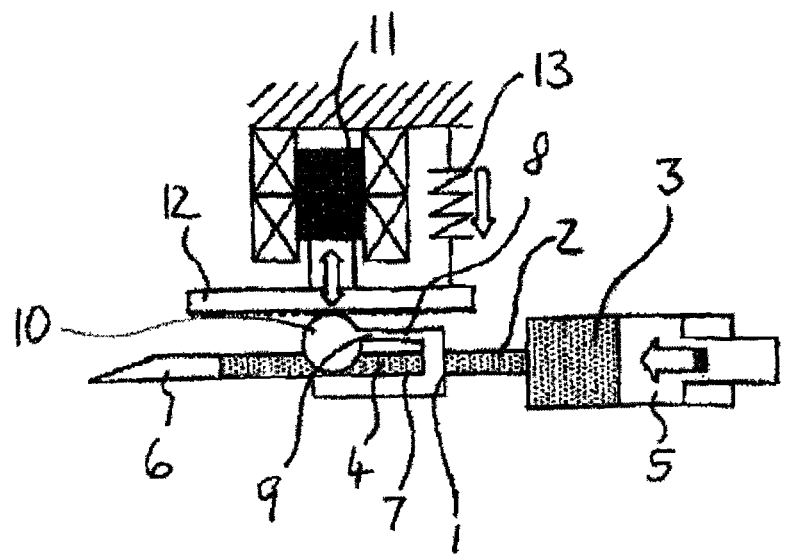

(51) Int. Cl.
*A61M 37/00* (2006.01)
*A61M 39/22* (2006.01)
*F16K 7/04* (2006.01)

(56) References Cited

U.S. PATENT DOCUMENTS

| | | | |
|---|---|---|---|
| 3,335,753 A | 8/1967 | Kiser | |
| 3,384,336 A * | 5/1968 | Pulman | 251/9 |
| 3,612,474 A * | 10/1971 | Strohl, Jr. | 251/9 |
| 3,822,052 A * | 7/1974 | Lange | 251/10 |
| 3,913,882 A | 10/1975 | Moulet | |
| 3,942,228 A * | 3/1976 | Buckman et al. | 251/4 |
| 4,053,135 A * | 10/1977 | Saliaris | 251/10 |
| 4,061,142 A * | 12/1977 | Tuttle | 604/34 |
| 4,077,601 A * | 3/1978 | Dick | 251/9 |
| 4,114,640 A * | 9/1978 | Forman | 137/381 |
| 4,429,852 A * | 2/1984 | Tersteegen et al. | 251/9 |
| 4,453,295 A * | 6/1984 | Laszczower | 251/10 |
| 4,501,405 A * | 2/1985 | Usry | 251/7 |
| 4,589,626 A * | 5/1986 | Kurtz et al. | 251/10 |
| 4,643,389 A * | 2/1987 | Elson et al. | 251/10 |
| 4,673,161 A * | 6/1987 | Flynn et al. | 251/10 |
| 4,787,406 A * | 11/1988 | Edwards et al. | 137/1 |
| 4,802,650 A * | 2/1989 | Stricker | 251/117 |
| 4,960,259 A * | 10/1990 | Sunnanvader et al. | 251/7 |
| 4,988,355 A * | 1/1991 | Leveen et al. | 606/158 |
| 5,035,399 A * | 7/1991 | Rantanen-Lee | 251/10 |
| 5,062,846 A * | 11/1991 | Oh et al. | 606/158 |
| 5,108,374 A * | 4/1992 | Lemieux | 604/167.01 |
| 5,203,056 A * | 4/1993 | Funk et al. | 24/543 |
| 5,401,256 A * | 3/1995 | Stone et al. | 604/250 |
| 5,522,806 A * | 6/1996 | Schonbachler et al. | 604/250 |
| 5,771,914 A * | 6/1998 | Ling et al. | 137/1 |
| 5,817,116 A * | 10/1998 | Takahashi et al. | 606/167 |
| 6,007,516 A * | 12/1999 | Burbank et al. | 604/288.03 |
| 6,079,691 A * | 6/2000 | Dragone | 251/7 |
| 6,089,527 A * | 7/2000 | Utterberg | 251/4 |
| 6,113,062 A * | 9/2000 | Schnell et al. | 251/10 |
| 6,161,812 A * | 12/2000 | Guala et al. | 251/10 |
| 6,196,519 B1 * | 3/2001 | Utterberg | 251/10 |
| 6,234,448 B1 * | 5/2001 | Porat | 251/10 |
| 6,386,505 B2 * | 5/2002 | Schob | 251/7 |
| 6,582,393 B2 * | 6/2003 | Sage, Jr. | 604/65 |
| 6,638,282 B2 * | 10/2003 | Ramsey et al. | 606/120 |
| 6,644,618 B1 * | 11/2003 | Balbo | 251/10 |
| 7,234,677 B2 * | 6/2007 | Zerfas | 251/10 |
| 7,260,932 B1 | 8/2007 | Klimowicz | |
| 8,025,645 B2 * | 9/2011 | Chesnin et al. | 604/250 |
| 8,262,639 B2 * | 9/2012 | Mathias | 604/403 |
| 8,328,763 B2 * | 12/2012 | Traversaz | 604/167.01 |
| 8,353,864 B2 * | 1/2013 | Davis | 604/67 |
| 8,469,331 B2 * | 6/2013 | Burbank et al. | 251/4 |
| 8,491,543 B2 * | 7/2013 | Stringham | 604/250 |
| 8,517,970 B2 * | 8/2013 | Mathias et al. | 604/6.15 |
| 2001/0049507 A1 * | 12/2001 | Ishida et al. | 604/250 |
| 2006/0015074 A1 * | 1/2006 | Lynn | 604/250 |
| 2009/0254034 A1 * | 10/2009 | Beck et al. | 604/118 |
| 2009/0302244 A1 * | 12/2009 | Wedel | 251/5 |

FOREIGN PATENT DOCUMENTS

| | | |
|---|---|---|
| DE | 4130601 | 4/1992 |
| DE | 19706513 | 8/1998 |
| DE | 69325591 | 2/2000 |
| DE | 10337484 | 3/2005 |
| DE | 202005009350 | 8/2005 |
| EP | 0455478 | 11/1991 |
| EP | 04770455 | 8/2004 |
| EP | 1699560 | 9/2006 |
| EP | 1882491 | 1/2008 |
| WO | WO2009149137 | 12/2009 |

* cited by examiner

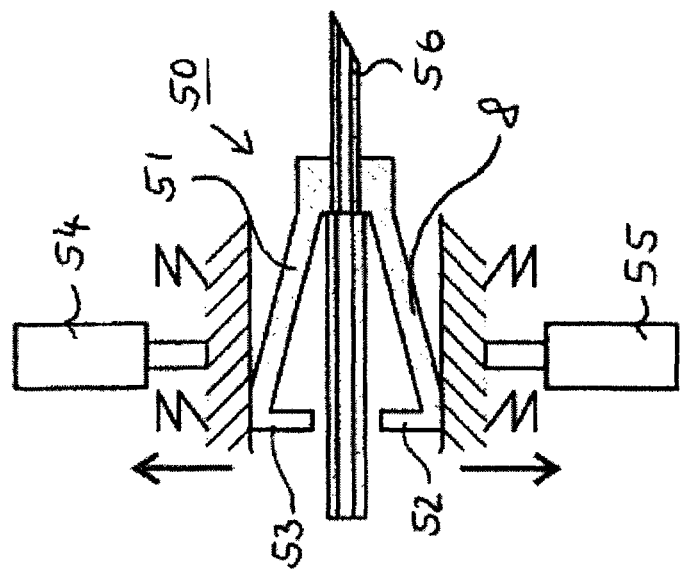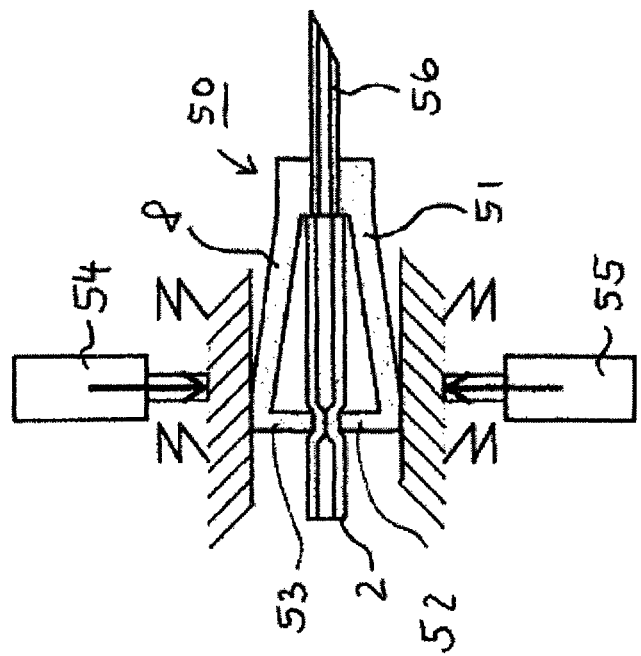
Fig. 5

VALVE DEVICE FOR CONTROLLING A FLOW OF A FLUID THROUGH A FLUID CHANNEL, ARRANGEMENT AND MULTI-WAY VALVE DEVICE

The invention relates to a valve device for controlling a flow of a fluid through a fluid channel, a system having at least one valve device and a multi-way valve device.

BACKGROUND OF THE INVENTION

Such valve devices are used to adjust and modify the volume flow of a fluid through a fluid channel. It is known in this context that the flow of the fluid through the channel is to be controlled by exerting pressure from the outside on a tube in which the fluid channel is formed, such that the pressure is adjusted as a function of a desired volume flow of the fluid through the channel.

In medical technology, dosing of volume flows takes place, for example, through micro-valves or directly through a corresponding pump with which the fluid to be dispensed is acted upon with pressure. Valves are used in medicine and in the cosmetic field, for example, in injection of medically and cosmetically active substances. In addition to the injection of substances for fat reduction or for injection beneath wrinkles, dosed dispensing of a substance is also necessary for application of ink for tattooing or permanent makeup in the cosmetic field. In addition to various vaccinations, medical applications also include, for example, mesotherapy. In these applications, in addition to the simple application of the media, simultaneous administration of multiple media is also provided, so that the media react with one another only after being applied.

The dosing of the fluid may be performed by means of a contact method or a noncontact method. The fluid-dispensing device thus either does or does not come in contact with the skin. Noncontact devices are also referred to as so-called dispensers. The process of delivering the fluid is itself known as dispensing, jetting or pulsing. This dosing serves to apply substances to the skin or in subsequent substance delivery systems (cf. EP 1 882 491, for example). Contacting may be understood as dosing onto or through a surface.

All these applications have in common the need for accurate dosing. Problems are often presented by chemical or fluid properties or particles or variable media.

The document DE 103 37 484 B4 describes a noncontact dosing system, in which a tube is squeezed at a high speed, so that a free-flying droplet of liquid is formed. Dosing frequencies of 50 Hz may be achieved in this way. The design here is an open system without a prepressure. The liquid fills the tube because of the capillary forces, but the maximum dosing quantity and dosing frequency are limited by this design. If there is a backpressure, functioning is very limited or impossible.

The document DE 693 25 591 T2 describes valve systems for switching a flow through flexible tubes. Two positions (bistable open/closed) are selected via a pivotable lever. The liquids should flow through the valve at the coupled flange of this construction, which is manufactured by casting and welding. Possible contamination of the liquid is not prevented, nor can this principle be used as a disposable part or for higher frequencies (>1 Hz).

The document U.S. Pat. No. 3,335,753 describes a valve device in which the flow through a flexible tube is adjustable by means of a squeeze element. The squeeze element is arranged on a rotatably mounted adjusting element, which is operable for displacement of the squeeze element, wherein a restoring force is supplied by a spring.

The document DE 20 2005 009 350 U1 discloses a hose clamp.

A tube valve is known from the document DE 1 707 336.

Document DE 2 353 624 describes a micro-control device for flow of liquids through flexible lines. With the known device, the flexible line is squeezed or released with the help of an operable lever arm.

The document EP 1 699 560 B1 describes one possibility for pipetting extremely small quantities, but is based essentially on a combination of traditional pipetting systems and the known PipeJet method, i.e., a tube deformation, embodied in this case as a pipette tip. It is thus possible here to dose only extremely small particles which fly freely through the air to their destination. This method cannot be used for injections because it is impossible to work at a backpressure.

The document DE 197 06 513 C2 describes a micro-dosing method based on a pressure chamber having a reservoir connection and a fluid outlet. The pressure chamber is reduced in size by a displacement mechanism, so that the fluid is forced to the outlet. A device for detecting the position of the displacement mechanism is essential here.

The document US 2010/0030152 A1 describes a therapeutic micro-needle system, in which multiple cannulas are used instead of one cannula.

SUMMARY OF THE INVENTION

The object of the invention is to provide improved technologies in combination with valve devices for controlling a flow of a fluid through a fluid channel, with which reliable control of the volume flow of the fluid is ensured, in particular even in high-frequency operation of the valve device.

This object is achieved according to the invention by a valve device for controlling a flow of a fluid through a fluid channel according to independent Claim 1. In addition, a system of at least one valve device according to independent Claim 16 and a multi-way valve device according to independent Claim 17 is also provided. Advantageous embodiments of the invention are the subject matter of dependent subsidiary claims.

The invention comprises the idea of a valve device for controlling a flow of a fluid through a fluid channel, comprising a tube of a flexible material, in which a section of a fluid channel is formed, a cantilevered arm which is designed to be reversibly displaceable on the valve component against a restoring force that is at least partially supplied by the cantilevered arm itself, a squeeze element, which is arranged on a distal end of the cantilevered arm for supporting the cantilevered arm on the valve component and is configured to control a flow of a fluid through the fluid channel by pressing against an outside surface of the tube, optionally up to the closing of the fluid channel, and an actuator which is assigned to the squeeze element and is configured to displace the squeeze element into various control positions, so that the pressure of the squeeze element on the outside surface of the tube and thereby the flow through the fluid channel can be regulated.

According to another aspect of the invention, a system having at least one valve device and a pressure-applying device, which is in fluid connection to the fluid channel, are provided, said pressure-applying device being configured so that a pressure can be applied to the fluid in the fluid channel.

Another aspect of the invention relates to a multi-way valve device having a plurality of valve devices for controlling the flow of a fluid through a fluid channel.

With the inventive valve device, there is the possibility of individually adjusting and regulating the volume flow through the fluid channel formed in the tube in accordance with the respective use requirements, including in particular a volume flow adjustment with high change frequencies or repeat frequencies. In one possible application, the displacement of the squeeze element produced by the actuator and the resulting change in flow through the tube can also be implemented by means of a corresponding repeating actuator movement, also at a high frequency. The actuator can be designed to conform to the respective use case, thus providing an adequate displacement path for the squeeze element. For example, the squeeze element may be displaced from a first position, in which the fluid channel in the tube is completely open, into a second position, in which the fluid channel is essentially closed. In one type of use with this embodiment, the valve device is used as a so-called closer. A reverse displacement of the squeeze element may also be provided, which then corresponds to an embodiment as a so-called opener.

The cantilevered arm may be designed in one or more parts. Thus, in one embodiment, multiple cantilevered arms are provided and may optionally cooperate.

In one embodiment, the actuator may act directly on the squeeze element, i.e., may couple directly to it in order to displace it. However, it is also possible to provide that the actuator acts on a different section of the cantilevered arm, i.e., couples to it, in order to pivot it against the restoring spring, so that the squeeze element is displaced on the distal end of the cantilevered arm.

The valve device may be used in any devices or device parts to control the flow of a fluid through the fluid channel in a tube. Use in a dosing unit is advantageous in particular, a medical or cosmetic active ingredient being delivered in a dosed manner with this dosing unit in the field of medicine or cosmetics. The dosing device may be embodied in a contact or noncontact design. For example, the dosing device may be integrated into an injection device to control the dosed delivery of an active ingredient under a backpressure. In this embodiment, the valve device is preferably downstream from a cannula that delivers the active ingredient. The cannula punctures the skin and can dispense the active ingredient at a predefined puncture depth, for example. The dosing device can thus be used in a method for dosed delivery of a fluid, in particular for injection into the human or animal body.

The relative movement between the guide and the valve component during use of the valve device in any dosing device, which is implemented as an injection device, for example, in which the fluid may also be dispensed against a backpressure, is preferably accomplished by means of manual operation or with the help of a drive. For example, devices for puncturing human or animal skin have drive mechanisms, which move a puncture device repetitively back and forth at a high frequency. This repetitive movement may then be used for the relative movement of the guide and the valve component to open and close the fluid channel in the tube. Such puncture devices are described in DE 299 19 199 U1, EP 1 495 782 and EP 1 618 915, for example. In addition, the following documents can be cited as examples: EP 1 743 673, EP 2 149 388 and EP 1 882 492. Other technologies may also be used as the drive mechanisms: pneumatics, lifting magnetic drive, drives having rotating motors and translation into a linear movement and a piezoelectric drive. The present invention may also be utilized in its various embodiments, in particular in conjunction with such puncture or injection devices.

According to a preferred further embodiment of the invention, the valve component is formed with a reversibly displaceable cantilevered arm on which the squeeze element is arranged. The cantilevered arm may be designed in one or more parts. For example, in one embodiment, multiple cantilevered arms, optionally cooperating with one another, may be provided. The reverse displacement is preferably accomplished here on the basis of a spring elastic design of the cantilevered arm. For example, the cantilevered arm is reversibly displaced by means of a pivoting movement of the cantilevered arm. In one embodiment, the squeeze element is formed on a distal end in relation to the base of the cantilevered arm, i.e., an area in which the cantilevered arm is mounted. The squeeze element is preferably formed on the cantilevered arm with a protrusion in the direction of the tube, which presses against the tube from the outside. A squeeze surface of the squeeze element assigned to the tube may have any surface contour, for example, a rounded surface, a spherical surface, or a surface with a squeeze edge, which is formed in the area of two surfaces running obliquely to one another. A combination of such surface contours may also be provided, in particular for optimizing the squeeze effect.

In an expedient embodiment of the invention, it is possible to provide for the cantilevered arm to extend along the tube and to optionally form an acute angle with the longitudinal direction of the tube. In one embodiment, the cantilevered arm runs essentially parallel to the longitudinal direction of the tube.

According to an advantageous embodiment of the invention, the actuator having at least one actuator element is selected from the group formed by actuator elements: electrical actuator element, magnetic actuator element, piezoelectric actuator element, pneumatic actuator element, mechanical actuator element and hydraulic actuator element.

According to a further embodiment of the invention, the actuator is formed with an actuating element which is configured to cause the displacement of the squeeze element in the various control positions by means of an actuator movement along one direction of movement which is essentially perpendicular to the longitudinal direction of the fluid channel, the guide is formed on a wall section. The wall section may be formed on a housing, for example, in which the valve component and the tube are accommodated. According to one embodiment, one housing part with the wall section formed thereon is moved in relation to the valve component during operation, and the guide section of the valve component slides along the guide on the housing part in this process, thereby displacing the squeeze element, which leads to a change in the flow through fluid channel. Conversely, it is possible to provide for the valve component to move in the housing in such a way that again the guide section slides along the guide formed on the housing part, which leads to a displacement of the squeeze element. Both the valve component and the wall section with the guide formed thereon may also move. In this embodiment or in others, it is possible to provide that the displacement of the squeeze element and thus the change in the flow through the fluid channel are repeated at a frequency between about 10 Hz and about 500 Hz, preferably between about 50 Hz and about 150 Hz. Alternatively, the use in a single-puncture mode is also conceivable, in which only a single puncture or a single injection is performed after manual triggering by the user.

In an advantageous embodiment of the invention, it is possible to provide for the valve component to be designed as a micro-valve component. In this way, the valve device is suitable for a micro-dosing device, for example.

A further embodiment of the invention may be provided, in which the squeeze element is designed to surround the tube at least partially.

According to a preferred further embodiment of the invention, the squeeze element is formed by a plurality of partial squeeze elements, which are arranged around the tube. In one embodiment, the squeeze elements are arranged on a shared base. It is possible to provide for the plurality of partial squeeze elements to be moved jointly by means of one or more actuators. This movement may take place similarly and/or simultaneously. In a preferred embodiment, the plurality of partial squeeze elements is formed in a rotationally symmetrical arrangement around the tube. In a further embodiment of the invention, the arrangement of the plurality of partial squeeze elements is embodied essentially according to a pressure-reducing mechanism.

In an expedient embodiment of the invention, it is possible to provide for the at least one part of the plurality of partial squeeze elements to be arranged so they are supported on one another at least in one end position. It is possible to provide here for individual partial squeeze elements to be supported on one another in the end position in which the fluid channel is partially or completely closed by squeezing of the tube, so that further closing of the fluid channel is no longer possible in one embodiment.

According to an advantageous embodiment of the invention, the cantilevered arm is designed to allow a displacement of the squeeze element for opening and at least partially closing the fluid channel in the tube with a high repeat frequency. In particular, such an embodiment provides for a restoring force that supports the high-frequency repetition of the displacement of the squeeze element. Such an embodiment may be formed with the above-mentioned cantilevered arm, for example.

A further embodiment of the invention preferably provides for the valve component to be embodied at least partially as an injection-molded part. Injection-molded parts are inexpensive and can also be manufactured by mass production. In these or other embodiments, it is possible to provide for the valve component to be embodied as a disposable product. In a further embodiment, the injection molding of the valve component may be embodied in a two-component injection molding process (2C injection molding). In one embodiment, the valve device having at least the one valve component, a tube section, the guide section and optionally a cannula connected to the tube section may be designed as a nonreturnable module or as a disposable module. Such a disposable module may be connected to a drive mechanism in a single step.

In one advantageous embodiment of the invention, it is possible to provide for the valve component to be arranged on the tube. In one embodiment, the valve component is designed to sit on the tube, preferably detachably. For example, the valve component may be arranged on the tube by means of an elastic clamping action, which is preferably provided by the squeeze element and the counterpart assigned to the squeeze element. According to a further embodiment, the valve component in this embodiment is designed with a tube guide, along which the tube runs in at least some sections when the valve component is arranged thereon. In one embodiment, the tube guide and the cantilevered arm having the squeeze element run essentially in parallel with the longitudinal direction of the tube, for example, above and below the tube.

A preferred further embodiment of the invention provides that the valve device has a disposable module, which is formed with at least the tube and the valve component. The disposable module preferably consists of these two elements.

In one expedient embodiment of the invention, it is possible to provide that the cantilevered arm is connected to a solid-state hinge.

An advantageous embodiment of the invention provides that the solid-state hinge is formed in a lever configuration.

An advantageous embodiment of the invention may provide that at least one coupling into which a tube end opens is formed on the valve component. The tube in the form of a length of tubing forms a uniform component together with the valve component, such that the tube is installed in the component so that the tube and the valve component are replaceable as a unit. Two such couplings may also be provided on the valve component, these two couplings being assigned to the two tube ends. Connecting pieces may be inserted or screwed into the coupling in order to connect the valve device, for example, to a nozzle, a dispenser, a micro-mixer, a syringe, a reservoir or the like.

In conjunction with the system having at least one valve device and a pressure-applying device, which is in fluid connection with the fluid channel, the integration of this system into a dosing device for dosed dispensing of a fluid may be provided, in particular a medicinal or cosmetic substance. Fluid dispensing may be performed here under the influence of a backpressure, which is important in particular in conjunction with injections. For example, such an injection device is used in combination with a device for tattooing or for creating permanent makeup. In this case, the dispensing of an ink is controlled by the valve device, but the dosing of another cosmetic active ingredient or a medicinal substance may also be provided.

In the case of a multi-way valve device, it may be provided in one embodiment that the fluid channels arranged side by side next to one another are adjusted with regard to the flow passing through them. In one embodiment, an integrated valve component, which serves to control the volume flow in multiple fluid channels, is provided. To this end, the integrated valve component has a plurality of squeeze elements, each being assigned to a tube with the fluid channel formed therein and displaceable by means of an assigned actuator. In a multi-way valve device, intersections between fluid channels may also be designed.

A series connection of multiple valve components may be suitable for increasing the dosing accuracy, inasmuch as the volume between the valve components, for example, contains a fluid under pressure and only the volume stored in between is dispensed by skillful opening and closing. For example, a corresponding valve may consist of tubes of different wall thicknesses or of tube-and-pipe combinations. The "storing" tube section need only be capable of storing energy, which maintains an excess pressure in this section (balloon with an inlet and an outlet). This is of interest for the purely mechanical embodiment in particular. It is possible to connect multiple valve components, which may be utilized to represent multi-way valves, for example (cf. FIG. 3). Other components may thus also be connected after the valve component.

The valve device may also be used for intake or suction. A combination of the two may also be provided, for example, intake and discharge in alternation or in multiple stages in succession (for example, in, in, out, out, out, out, etc.). This may be used for tattoo removal, for example, during which active ingredients are injected into the tattoo and the tattoo pigments are removed by suction. This method of tattoo removal is described as such in the document WO 2005/020828, for example.

One advantage of the invention is the possibility that pre-dosed or variable and/or crystallizing/drying media may be dosed without damaging the system or having to clean it because the fluid transport takes place only in a system that is easy to change.

The valve component and the valve device may be used in a liquid handling system, for example, or in a micro-mixer.

DESCRIPTION OF PREFERRED EXEMPLARY EMBODIMENTS OF THE INVENTION

Figure 2:
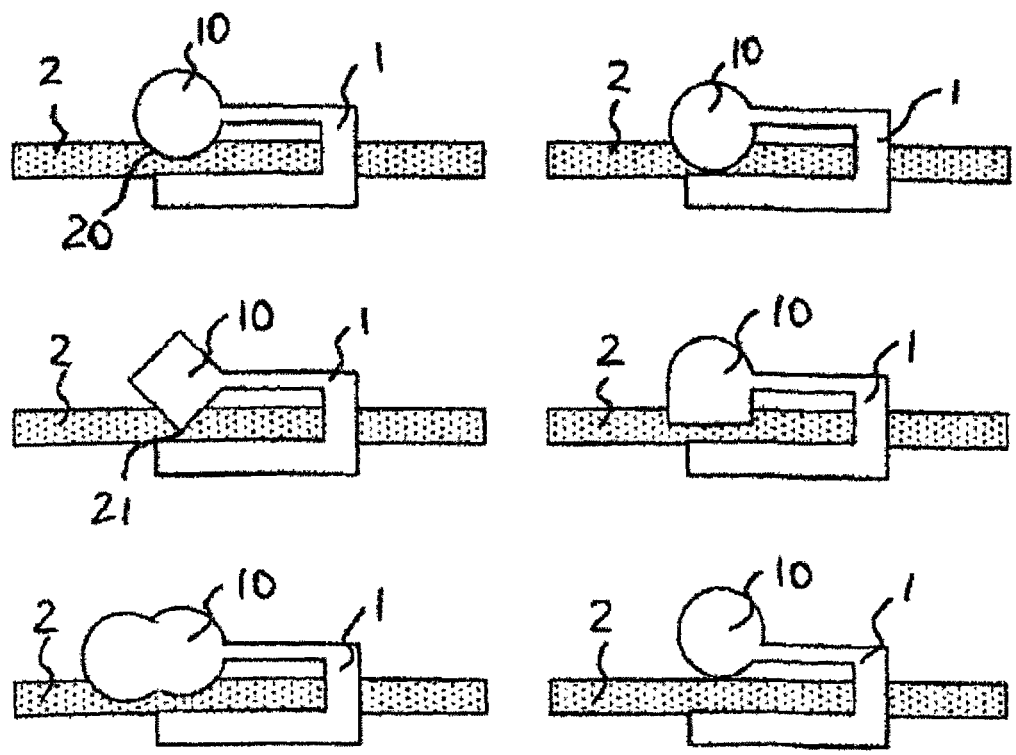
Figure 3:
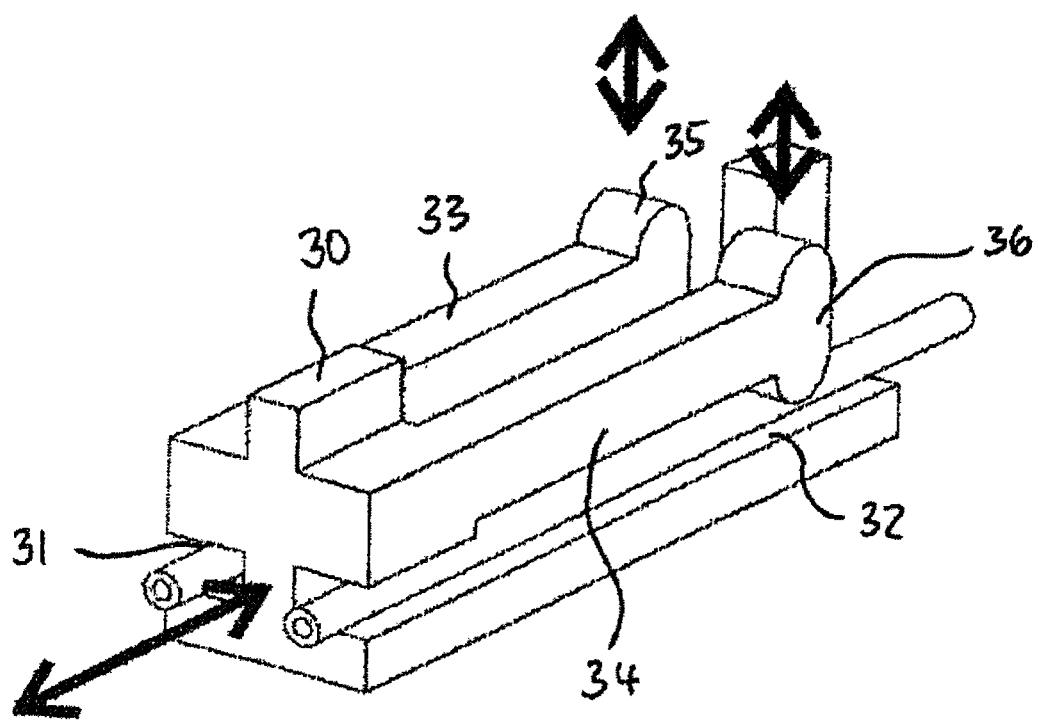
Figure 4:
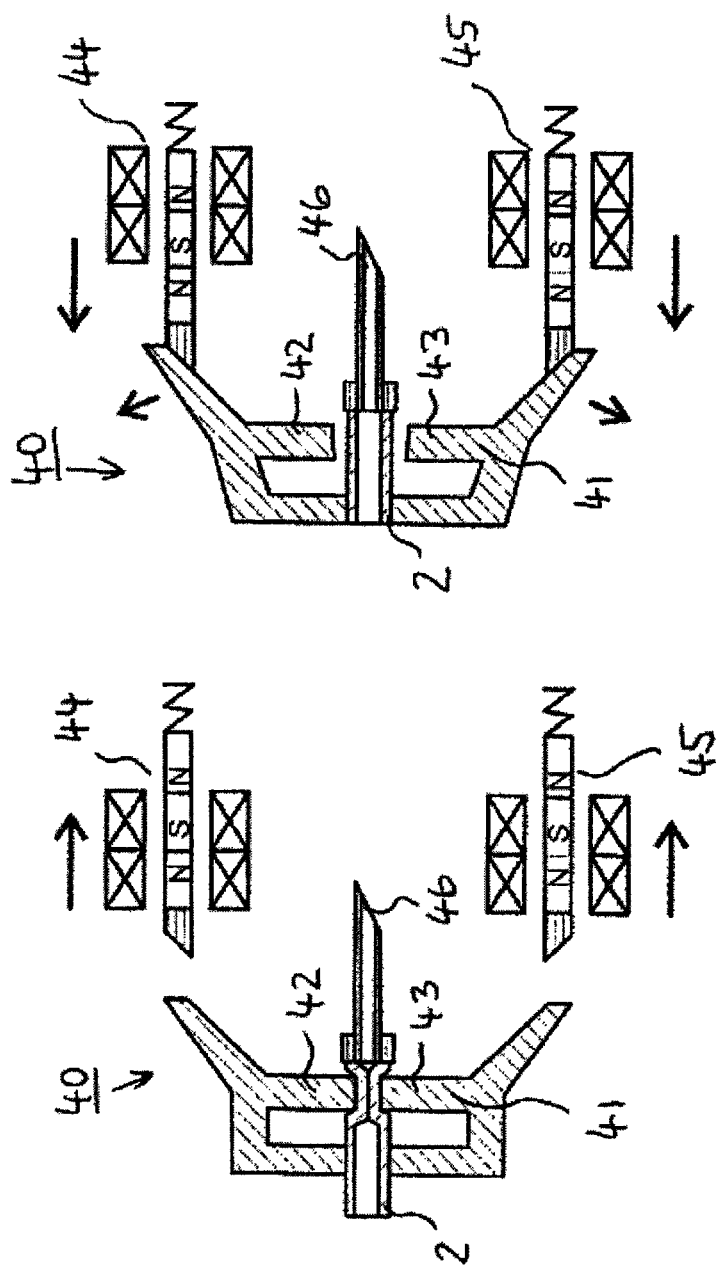
Figure 6:
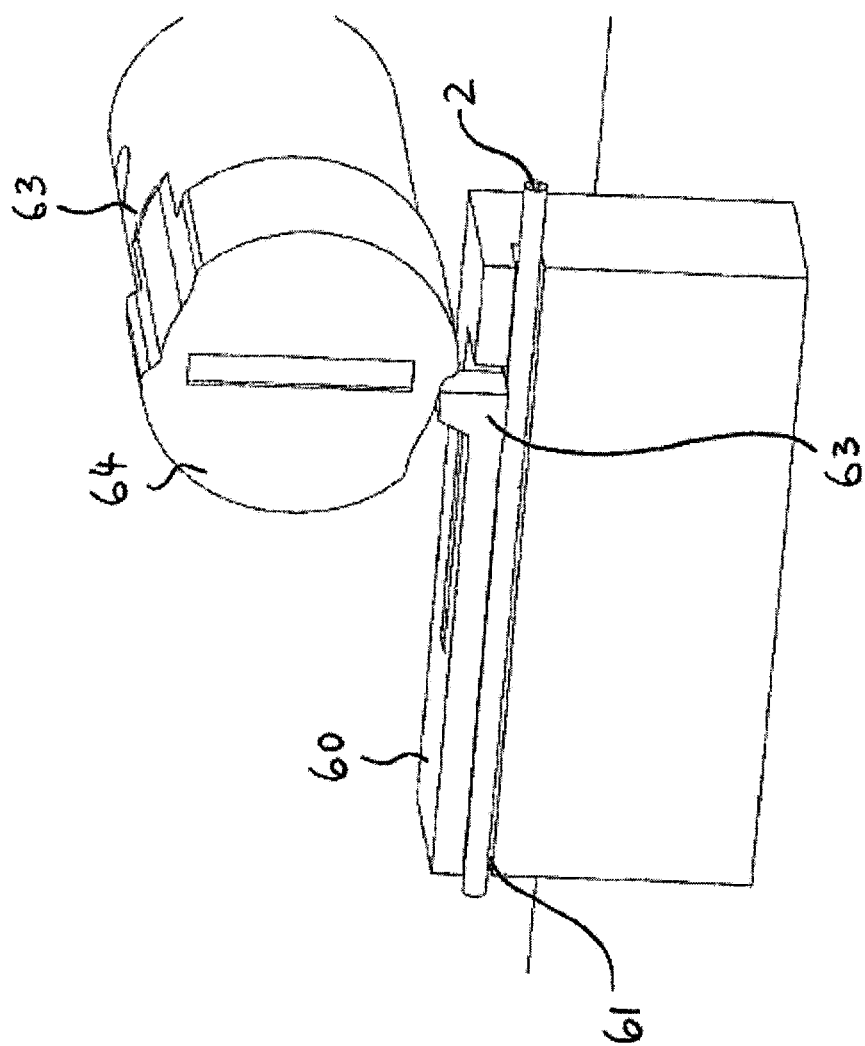
Figure 7:
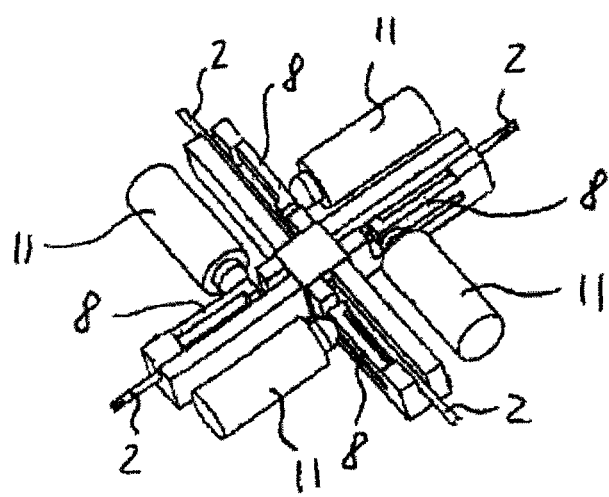
Figure 8:
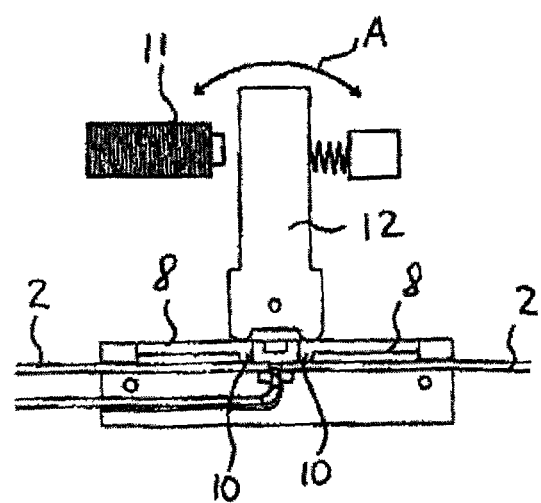
Figure 9:
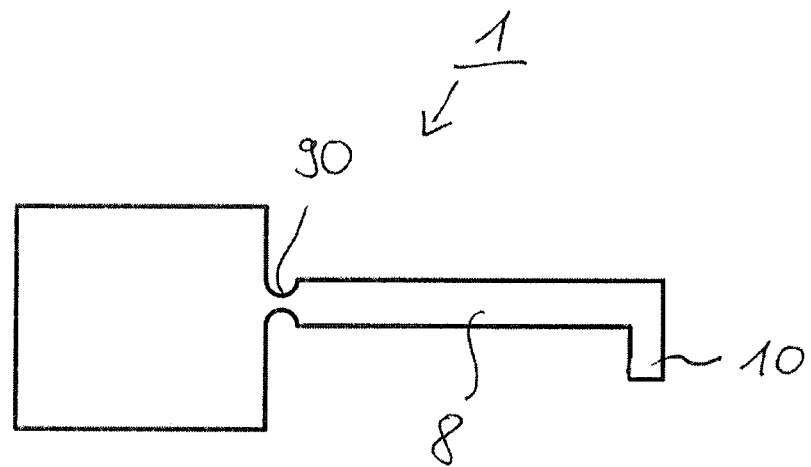
Figure 10:
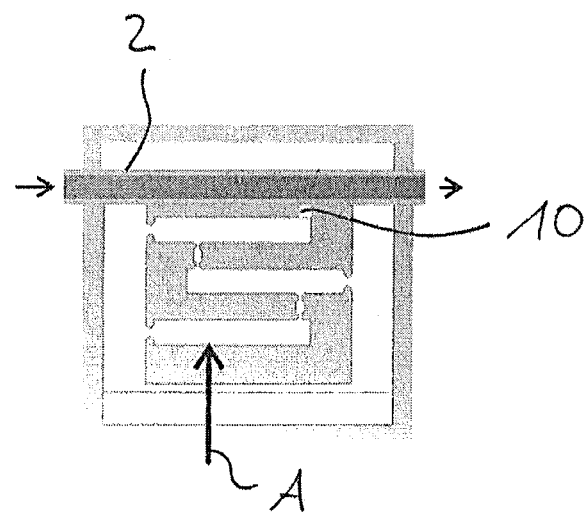
Figure 11:
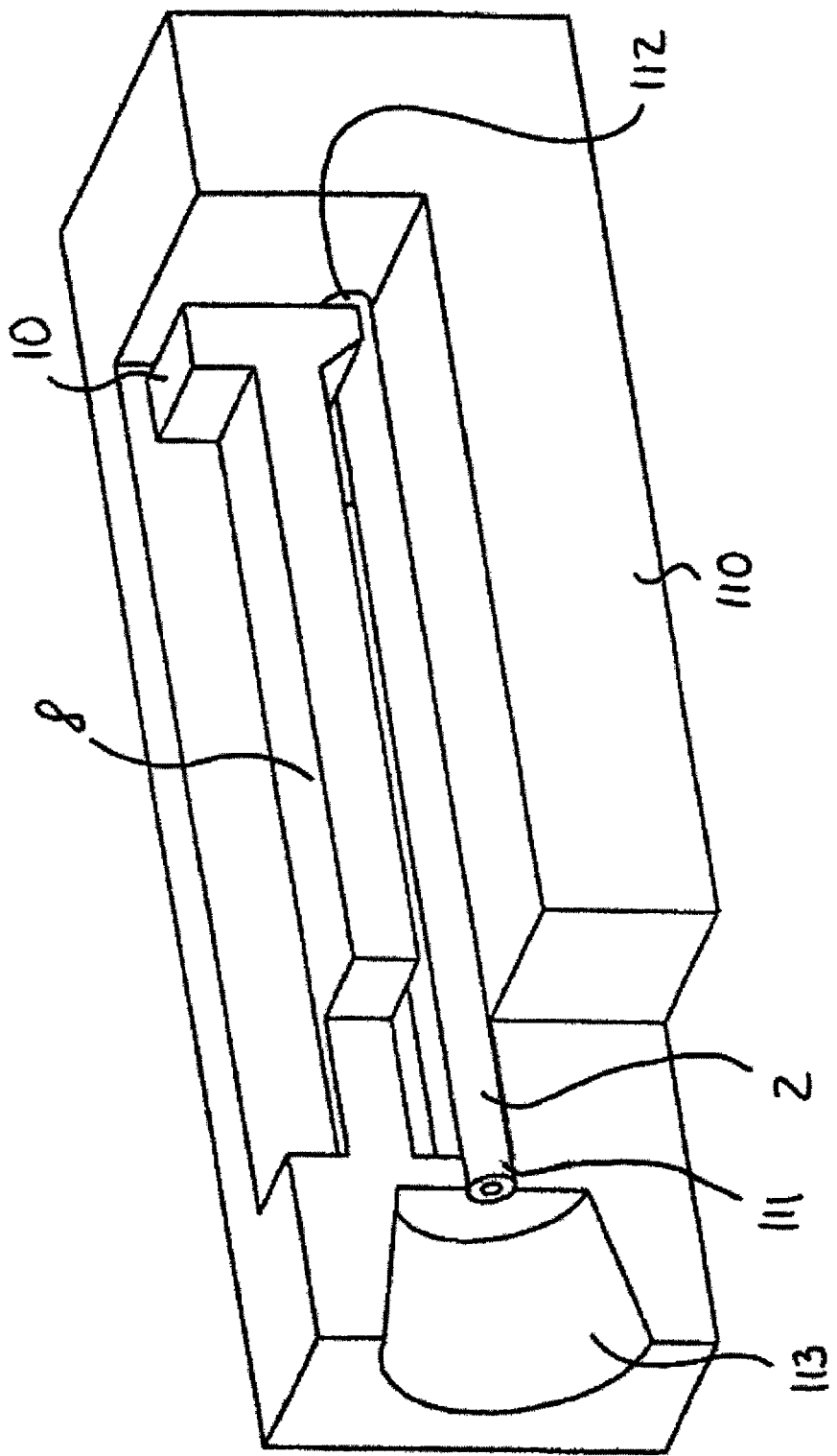
Figure 12:
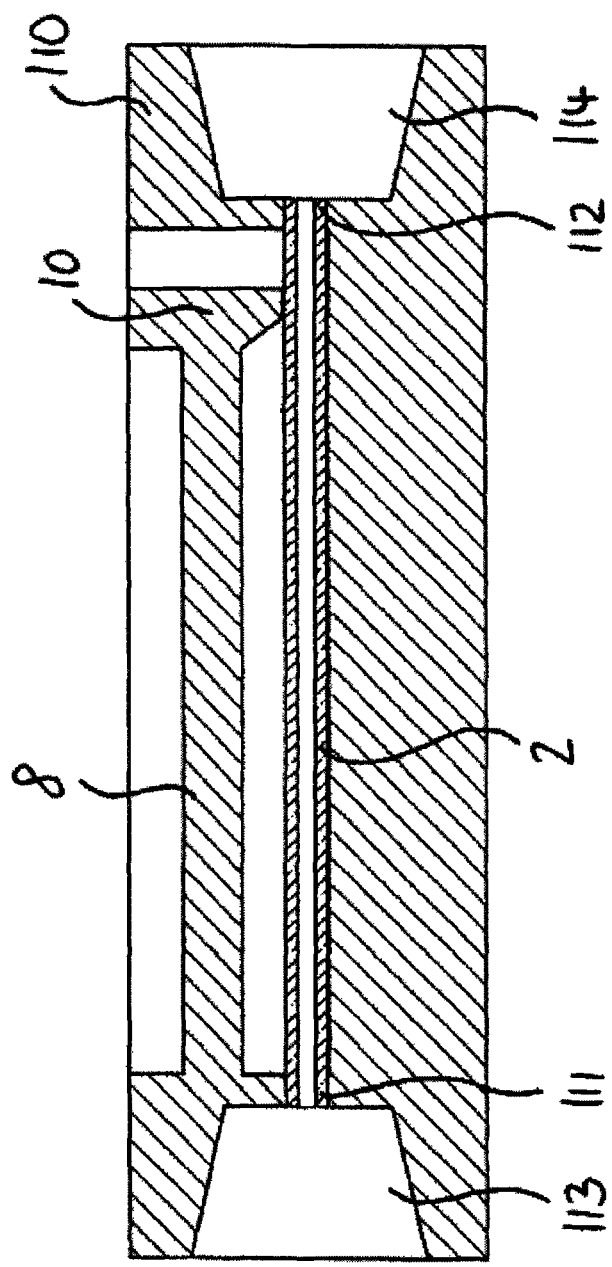

The invention is explained in greater detail below on the basis of preferred exemplary embodiments with reference to drawings in figures, in which FIG. 1 shows a schematic diagram of a system having a valve device, FIG. 2 shows multiple embodiments of a valve component, FIG. 3 shows a schematic diagram of a multi-way valve device, in which two fluid channels run parallel to one another, FIG. 4 shows a schematic diagram of a system having another valve device, FIG. 5 shows a schematic diagram of a valve device according to another embodiment, FIG. 6 shows a perspective view of a valve device in another embodiment, FIG. 7 shows a schematic diagram of another multi-way valve device, FIG. 8 shows a schematic diagram of an application with a valve device in a multi-way embodiment, FIG. 9 shows a schematic diagram of a valve component in which the squeeze element is arranged on the distal end of the cantilevered arm, FIG. 10 shows a valve device integrated into a solid-state system, FIG. 11 shows a schematic diagram of a valve device, in which the tube is arranged in a valve body, such that the tube ends are coupled to couplings, and FIG. 12 shows a sectional diagram through the valve device from FIG. 11.

FIG. 1 shows a schematic diagram of a system having a valve component 1, which is arranged on a tube 2, in which a fluid channel 4 for a fluid 3 is formed, through which the fluid 3 from a reservoir 5 which is acted upon by pressure reaches a cannula 6, where the fluid is dispensed in dosed form. The reservoir 5 may be, for example, a reservoir for ink, which is used to form a tattoo or permanent makeup. In another embodiment, the reservoir may also contain, for example, a substance for injection under wrinkles.

The valve component 1 is formed with a tube guide 7 on which the tube 2 rests. A cantilevered arm 8 is formed opposite the tube guide 7. A squeeze element 10 is arranged on the distal end 9 of the cantilevered arm 8, pressing on the tube 2 from the outside. The squeeze element 10 is displaced along a direction of movement, which runs essentially across the longitudinal direction of the tube 2, in that an actuator 11 with an operating element 12 cooperates with the squeeze element 10. In the embodiment in FIG. 1, the squeeze element 10 is pressed onto the tube 2 against a restoring force of the cantilevered arm, to adjust the flow of the fluid through the tube 2. The operating element 12 is also displaced against a spring force 13 in the embodiment shown here.

Various types of actuators can be used, for example, a pneumatic, hydraulic, electric, magnetic or piezoelectric actuator element.

The volume flow of a known medium can be adjusted by means of the respective squeeze element 10 by regulating the applied pressure, the opening width and/or the opening time. These parameters influence the amount of dosable substances and/or viscosities. In principle, any liquid and gaseous substances with particles that are not too large in comparison with the inside diameter of the tube can be dosed in this way.

The respective clamping or squeezing device may be operated purely mechanically by operation the clamping device driven by an actuator, which causes the clamp formed by the squeeze element to be opened and closed. The clamping action can be reset in particular via the elastic deformation (restoring force of the cantilevered arm 8) and/or restoring forces of the tube and/or by the pressure of the medium in the tube on the tube wall. Dosing can be performed at high frequencies in this way.

The valve component 1 with the squeeze element 10 may be fixedly connected to the tube 2 or attached to it subsequently. In the latter case, the valve device may be embodied as a multi-way valve. Because of its low manufacturing cost, for example, when made of plastic by the injection molding method, and its better handleability, disposable use is to be given preference but variants comprised of other materials, such as metal, composite materials or the like are also possible.

In its various embodiments, the valve component may operate as an opener or a closer. A continuous change in the volume flow may be achieved. The pressure may be applied to the tube from one or more sides. One-sided is understood here to mean that the volume cross section is limited from one side; for example, the squeeze element presses from one side on a tube that is fixed on a substrate with respect to the squeeze element. In the two-sided case, the valve component to the principle of tongs or forceps is conceivable according (cf. FIG. 4), where the clamping jaws are guided opposite one another.

FIG. 2 shows multiple embodiments of the valve component 1, where the squeeze element 10 is formed with different geometric designs accordingly. In particular a surface form in a squeeze section 20 of the squeeze element 10 facing the tube 2 is designed in a different manner. A rounded surface, a spherical surface, a planar surface and a surface area having a squeeze edge 21 belong here.

FIG. 3 shows a schematic diagram of a multi-way valve device in which a double-valve component 30 having parallel tube guides 31, 32 is formed. A respective squeeze element 35, 36 which presses on the respective tube from the outside is formed on the respective cantilevered arms 33, 34.

FIG. 4 shows a schematic diagram of a valve component 40 in a closed position and in an opened position (cf. left and right sides in FIG. 4), in which a squeeze element 41 with clamping jaws 42, 43 is formed, these being formed on the respective cantilevered arm 8 and being activated with the help of a respective actuator 44, 45. The flow through the tube 2 to a cannula 46 is enabled or closed by operation of the clamping jaws 42, 43.

FIG. 5 shows a schematic diagram with a valve component 50, in which a squeeze element 51 is also formed with two clamping jaws 52, 53, which are formed on the respective cantilevered arm 8 and are displaced with the help of the respective actuators 54, 55 to enable or to suppress the flow through the tube 2 to a cannula 56.

For the actuators 42, 43 and/or 52, 53 shown in FIGS. 4 and 5, actuators based on different operative principles may be used, for example, electrical, pneumatic, mechanical or piezoelectric actuators.

FIG. 6 shows a perspective diagram of a valve device in another embodiment, in which a valve component is formed with a guide 61 in which the tube 2 is arranged. A respective squeeze element 62 is on the outside of the tube 2 and is displaced repetitively with the help of a mechanical actuator

63, in that a rotating component 64 rotates on the mechanical actuator 63. The squeeze element is pressed more or less against the tube 2 because of the surface contour of the rotary component 64, thereby regulating the flow through the tube 2.

FIG. 7 shows a schematic diagram of a system having several valves, each of which is preferably formed with a valve component 1 in one of the embodiments described previously as well as a respective actuator 11. A four-way valve with actuators 11 is formed.

FIG. 8 shows a schematic diagram of a system having a valve device in a multi-way embodiment, in which the squeeze elements 10 are operated in alternation, in that the operating element 12 of the actuator 11 is pivoted (cf. arrow A in FIG. 8).

In preliminary investigations, dispensing frequencies of up to 400 Hz have been achieved. The dosed droplets were separated completely from the end of the tube in either the horizontal position or in the vertical position. Distilled water was used as the test fluid at a pressure of 2 bar ad a tube diameter of 0.7×0.3 mm (outside to inside). Clean separation of the individual droplets was verified using a high-speed camera at a recording frequency of 3,400 Hz. The test setup was made of plastic on a miniaturized scale. The dimensions of the functioning valve device were 4×4×15 mm.

Application fields are found in injection of medicinal and cosmetic substances in particular. Integration into a bundle of complete needles of a puncture or injection device may be provided, just as it is also possible to operate multiple cannulas simultaneously. Examples of cosmetic treatments that can be mentioned include carboxy therapy, i.e., injection of $CO_2$, for example, for fat reduction, injections beneath wrinkles at depths of 1.0 to 4.0 mm using a wide variety of media, tattooing and tattoo removal (cf. EP 04 770 455, which refers only to superficial suction removal there) at depths of 1.0-3.5 mm or application of permanent makeup at depths of 0.3-1.0 mm. Suction removal of skin is conceivable in general for both cosmetic and medical application. Purely medical applications include not only various vaccinations at depths of 0.2-0.6 mm but also mesotherapy at depths of 0.2-10 mm.

The following list represents a selection of possible substances that may be applied: hyaluronic acid, vitamins, Q10, vaccines, therapeutic antibodies, cancer antibodies, diabetes therapeutic agents, hormones, cytokines, biochemical or biological signal substances, antioxidants, hair growth agents, hair growth inhibitors, mineral substances to improve skin tone and skin metabolism, enzymes, coenzymes, amino acids, nucleic acids, inert pigment particles, inert skin fillers, nerve-activating ingredients such as botox or bacterial toxin, diabetic control agents such as color-changing particles, which depend on the glucose level.

For all applications, in addition to the simple administration of media, this simultaneous administration of multiple media is also conceivable; these media should react with one another only after the injection, for example. Some of the applications have in common the introduction or removal of a wide variety of media at a defined depth and/or at a certain point in time. The importance of the precise depth of a vaccination can be seen clearly in the intracutaneous vaccination technique in particular. The active ingredient to be administered as a vaccine loses a substantial portion of its effect when the target depth is exceeded by more than 15%.

In addition to packaging extremely small quantities of medium, such as expensive medications, the desired mixing ratio can be adjusted extremely easily, for example, with several different tube diameters.

Especially in fields such as vaccination technique, even reagents that are very difficult to handle can be used easily because they can be used in a closed container with a valve and therefore do not come in contact with the actual dispenser. It is thus possible to avoid tedious cleaning of the devices.

It is also conceivable to use a sealing liquid, comparable to a cork, for example, a hydrophilic active ingredient and a hydrophobic sealing substance to thus prevent the substance administered from running off. A high-viscosity sealing substance may also be used for this purpose. Alternatively, the closure of the skin may be implemented by coagulation with HF, laser or other thermal effects.

The present invention in its various embodiments can be combined with other technologies, for example, with measurement of the depth of skin layers and automatic adjustment of the optimum puncture depth of the needle. The substances may be injected accurately into the predefined skin strata. The measurement and puncture depth technologies are described in document EP 188 2493, for example.

Based on the simple design, the numerous operating variants and the small design height, the invention can be integrated into a variety of different products with minimal effort.

FIG. 9 shows a schematic diagram of a valve component 1, where the squeeze element 10 is arranged on the distal end of the cantilevered arm 8, and the proximal end of the cantilevered arm 8 is coupled to a solid-state hinge 90. The solid-state hinge 90 has the advantage that it minimizes the forces required to operate the valve. Solid-state hinges in general involve areas of the cantilevered arm 8 which have a reduced stiffness, so that articulated points or kink points are formed. Much shorter levers can be used with the cantilevered arm 8 by means of a solid-state hinge, which supports further miniaturization of the valve device and integration in complex liquid handling systems.

A more extensive miniaturization is possible by presqueezing the tube. For example, if a tube with the dimensions 0.7×0.3 mm is squeezed by 0.2 mm, then the achievable volume flow is approximately 90% of the undisturbed cross section. This reduces the required lever travel from 0.35 mm to 0.15 mm.

Solid-state hinges can be integrated easily during production by injection molding by designing the molds accordingly. Production by micro-milling or eroding is also possible with metallic materials.

The valve device can also be integrated directly into a solid-state system, which is illustrated in FIG. 10, for example. The squeeze element 10 is on the tube 2, through which a liquid flows. A fixed joint system 100 can be operated by means of an actuator, which is diagrammed schematically with the arrow A in FIG. 10. The embodiment shown here illustrates an implementation of a force-distance translation, in which the squeeze element 10 is formed on the lowest lever. The lever design shown in FIG. 10 with the tube 2 included can be produced inexpensively by injection molding, for example.

FIG. 11 shows a schematic diagram of a valve device, in which the tube 2 in the form of a length of tubing is arranged in a valve component 110 and is installed in it so that the tube 2 has tube ends 111, 112, which are surrounded by the valve component 110 at the ends, through which the valve device can be connected to coupling pieces or connections (not shown) which are then preferably inserted or screwed into the couplings 111, 112. The cantilevered arm 8 with the squeeze element 10 is formed in one piece on the body of the valve component 110. The valve device can thus be replaced completely as a unit in one step, which greatly reduces the replacement time and pursues the idea of a modular construction kit for various "fluid components."

FIG. 12 shows a sectional diagram of the valve device from FIG. 11.

The features of the invention disclosed in the above description, the claims and the drawing may be important individually as well as in any combination for the implementation of the invention in its various embodiments.

The invention claimed is:

1. A valve device for controlling a flow of a fluid through a fluid channel, comprising:
   a tube of flexible material in which a section of a fluid channel is formed,
   a valve component assigned to the tube,
   a first cantilevered arm, which is designed to be reversibly displaceable on the valve component against a restoring force which is supplied by the first cantilevered arm at least partially by itself, the first cantilevered arm projecting from a proximate end to a distal end and providing at the distal end a mounting surface that faces towards an outer surface of the tube,
   a first squeeze element, which is formed on the mounting surface of the first cantilevered arm and projecting outwardly from the mounting surface is configured to control a flow of a fluid through the fluid channel by pressing against an outside surface of the tube,
   a first actuator which is assigned to the first squeeze element and is configured to displace the first squeeze element in various control directions against the restoring force on the first cantilevered arm, so that the pressure of the first squeeze element on the outside surface of the tube and thereby the flow through the fluid channel is regulated,
   a second cantilevered arm, which is designed to be reversibly displaceable on the valve component against a restoring force which is supplied by the second cantilevered arm at least partially by itself, the second cantilevered arm projecting from a proximate end to a distal end and providing at the distal end a mounting surface that faces towards an outer surface of the tube,
   a second squeeze element, which is formed on the mounting surface of the second cantilevered arm and projecting outwardly from the mounting surface, is arranged on an opposing side of the tube in relation to the first squeeze element and configured to control a flow of a fluid through the fluid channel by pressing against an outside surface of the tube, and
   a second actuator which is assigned to the second squeeze element and is configured to displace the second squeeze element in various control directions against the restoring force on the second cantilevered arm, so that the pressure of the second squeeze element on the outside surface of the tube and thereby the flow through the fluid channel is regulated.

2. The valve device according to claim 1, characterized in that the cantilevered arm extends along the tube and forms an acute angle with the longitudinal direction of the tube.

3. The valve device according to claim 1, characterized in that at least one of the first actuator and the second actuator having at least one actuator element is selected from the following group of actuator elements: electrical actuator element, magnetic actuator element, piezoelectric actuator element, pneumatic actuator element, mechanical actuator element and hydraulic actuator element.

4. The valve device according to claim 1, characterized in that at least one of the first actuator and the second actuator is designed with an operating element, which is configured to cause the corresponding squeeze element to be displaced into the various control positions by means of an actuator movement along a direction of movement, which runs perpendicular to the longitudinal direction of the fluid channel.

5. The valve device according to claim 1, characterized in that the valve component is designed as a micro-valve component.

6. The valve device according to claim 1, characterized in that the first cantilevered arm is designed to allow a displacement of the first squeeze element for opening and at least partially closing the fluid channel in the tube at a frequency on the order of 400 Hertz.

7. The valve device according to claim 1, characterized in that the valve component is designed to allow at least partial closing of the fluid channel in the tube.

8. The valve device according to claim 1, characterized in that the valve component is arranged on the tube.

9. The valve device according to claim 1, characterized by a disposable module, which is formed at least with the tube and with the valve component.

10. The valve device according to claim 1, characterized in that the cantilevered arm is coupled to a solid-state hinge.

11. The valve device according to claim 10, characterized in that the solid-state hinge is formed in a lever arrangement.

12. The valve device according to claim 1, characterized in that at least one coupling is formed on the valve component, with one tube end opening into said coupling.

13. A system for controlling a flow of a fluid through a fluid channel, comprising:
   a tube of flexible material in which a section of a fluid channel is formed;
   a valve component assigned to the tube;
   a first cantilevered arm, which is designed to be reversibly displaceable on the valve component against a restoring force which is supplied by the first cantilevered arm at least partially by itself, the first cantilevered arm projecting from a proximate end to a distal end and providing at the distal end a mounting surface that faces towards an outer surface of the tube;
   a first squeeze element, which is formed on the mounting surface of the first cantilevered arm and projecting outwardly from the mounting surface is configured to control a flow of a fluid through the fluid channel by pressing against an outside surface of the tube,
   a first actuator which is assigned to the first squeeze element and is configured to displace the first squeeze element in various control directions against the restoring force on the first cantilevered arm, so that the pressure of the first squeeze element on the outside surface of the tube and thereby the flow through the fluid channel is regulated;
   a second cantilevered arm, which is designed to be reversibly displaceable on the valve component against a restoring force which is supplied by the second cantilevered arm at least partially by itself, the second cantilevered arm projecting from a proximate end to a distal end and providing at the distal end a mounting surface that faces towards an outer surface of the tube,
   a second squeeze element, which is formed on the mounting surface of the second cantilevered arm and projecting outwardly from the mounting surface, is arranged on an opposing side of the tube in relation to the first squeeze element and configured to control a flow of a fluid through the fluid channel by pressing against an outside surface of the tube, and
   a second actuator which is assigned to the second squeeze element and is configured to displace the second squeeze element in various control directions against the restoring force on the second cantilevered arm, so that the pressure of the second squeeze element on the outside surface of the tube and thereby the flow through the fluid channel is regulated, and a pressure-applying device, which is in fluid connection with the fluid channel and is configured to apply a pressure to the fluid in the fluid channel.

14. A multi-way valve device, comprising:

a plurality of valve devices, each of the valve devices in the plurality of valve devices includes

- a tube of flexible material in which a section of a fluid channel is formed;
- a valve component assigned to the tube;
- a first cantilevered arm, which is designed to be reversibly displaceable on the valve component against a restoring force which is supplied by the first cantilevered arm at least partially by itself, the first cantilevered arm projecting from a proximate end to a distal end and providing a mounting surface at the distal end such that the mounting surface faces towards an outer surface of the tube;
- a first squeeze element, which is formed on the mounting surface of the first cantilevered arm and projecting outwardly from the mounting surface is configured to control a flow of a fluid through the fluid channel by pressing against an outside surface of the tube; and
- a first actuator which is assigned to the first squeeze element and is configured to displace the first squeeze element in various control directions against the restoring force on the first cantilevered arm, so that the pressure of the first squeeze element on the outside surface of the tube and thereby the flow through the fluid channel is regulated;
- a second cantilevered arm, which is designed to be reversibly displaceable on the valve component against a restoring force which is supplied by the second cantilevered arm at least partially by itself, the second cantilevered arm projecting from a proximate end to a distal end and providing at the distal end a mounting surface that faces towards an outer surface of the tube;
- a second squeeze element, which is formed on the mounting surface of the second cantilevered arm and projecting outwardly from the mounting surface, is arranged on an opposing side of the tube in relation to the first squeeze element and configured to control a flow of a fluid through the fluid channel by pressing against an outside surface of the tube; and
- a second actuator which is assigned to the second squeeze element and is configured to displace the second squeeze element in various control directions against the restoring force on the second cantilevered arm, so that the pressure of the second squeeze element on the outside surface of the tube and thereby the flow through the fluid channel is regulated.

* * * * *